United States Patent [19]

Feldinger et al.

[11] Patent Number: 5,033,438
[45] Date of Patent: Jul. 23, 1991

[54] METHOD AND DEVICE FOR IMPROVING THE EXHAUST-GAS BEHAVIOR OR MIXTURE-COMPRESSING INTERNAL COMBUSTION ENGINES

[75] Inventors: Martin Feldinger, Königstein; Joachim Tambosi; Uwe März, both of Schwalbach/Ts., all of Fed. Rep. of Germany

[73] Assignee: VDO Adolf Schindling AG, Frankfurt am Main, Fed. Rep. of Germany

[21] Appl. No.: 577,646

[22] Filed: Aug. 31, 1990

[30] Foreign Application Priority Data

Aug. 31, 1989 [DE] Fed. Rep. of Germany ....... 3928860

[51] Int. Cl.$^5$ ............................................ F02D 41/14
[52] U.S. Cl. .................................................. 123/489
[58] Field of Search ............... 123/440, 486, 488, 489, 123/589; 364/431.05, 431.12

[56] References Cited

U.S. PATENT DOCUMENTS

| | | | |
|---|---|---|---|
| 3,906,207 | 9/1975 | Rivere et al. | 123/489 X |
| 4,019,474 | 4/1977 | Nishimiya et al. | 123/440 |
| 4,116,170 | 9/1978 | Anzai | 123/440 |
| 4,337,745 | 7/1982 | Pomerantz | 123/440 |
| 4,917,067 | 4/1990 | Yoshida | 123/489 X |
| 4,964,390 | 10/1990 | Kameta et al. | 123/489 |

FOREIGN PATENT DOCUMENTS

| | | |
|---|---|---|
| 0067931 | 12/1982 | European Pat. Off. . |
| 0123064 | 10/1984 | European Pat. Off. . |
| 0305998 | 3/1989 | European Pat. Off. . |
| 2355437 | 1/1978 | France . |
| 2570127 | 3/1986 | France . |
| 2193327 | 2/1988 | United Kingdom . |

*Primary Examiner*—Willis R. Wolfe
*Attorney, Agent, or Firm*—Martin A. Farber

[57] ABSTRACT

A method for improving the exhaust-gas behavior of mixture-compressing internal combustion engines. The output signal of an oxygen measurement probe arranged in the exhaust gas channel of the internal combustion engine is divided within the voltage region in question into a number of sections and a corrected voltage value is stored in a memory for each section.

8 Claims, 9 Drawing Sheets

| mV | λ | digital values in the memory |
|---|---|---|
| 3 | 1.2 | 0 |
| 6.5 | 1.2 | 0 |
| 10 | 1.2 | 0 |
| 13.5 | 1.2 | 0 |
| 17 | 1.2 | 0 |
| 20.5 | 1.2 | 0 |
| 24 | 1.2 | 0 |
| 27.5 | 1.2 | 0 |
| 31 | 1.2 | 0 |
| 34.5 | 1.2 | 0 |
| 38 | 1.2 | 0 |
| 41.5 | 1.168 | 20 |
| 45 | 1.137 | 40 |
| 48.5 | 1.117 | 53 |
| 52 | 1.104 | 61 |
| 55.5 | 1.09 | 70 |
| 59 | 1.076 | 79 |
| 62.5 | 1.062 | 88 |
| 66 | 1.051 | 95 |
| 69.5 | 1.043 | 100 |
| 73 | 1.0375 | 104 |
| 76.5 | 1.0315 | 107 |
| 80 | 1.028 | 110 |
| 83.5 | 1.0255 | 111 |
| 87 | 1.0225 | 113 |
| 90.5 | 1.02 | 115 |
| 94 | 1.018 | 116 |
| 97.5 | 1.0165 | 117 |
| 101 | 1.0155 | 118 |
| 104.5 | 1.014 | 119 |
| 108 | 1.013 | 119 |
| 111.5 | 1.012 | 120 |
| 115 | 1.0115 | 120 |
| 118.5 | 1.0105 | 121 |
| 122 | 1.01 | 121 |
| 125.5 | 1.009 | 122 |
| 129 | 1.0085 | 122 |
| 132.5 | 1.008 | 122 |
| 136 | 1.0076 | 1235 |
| 139.5 | 1.0073 | 123 |
| 143 | 1.0069 | 1235 |
| 146.5 | 1.0066 | 123 |
| 150 | 1.0062 | 1245 |
| 153.5 | 1.0059 | 124 |
| 157 | 1.0055 | 1245 |
| 160.5 | 1.0052 | 124 |
| 164 | 1.0048 | 1245 |
| 167.5 | 1.0045 | 125 |

Fig. 3a

| mV | λ | digital values in memory |
|---|---|---|
| 171 | 1.004 | 125 |
| 174.5 | 1.004 | 125 |
| 178 | 1.004 | 125 |
| 181.5 | 1.004 | 125 |
| 185 | 1.003 | 126 |
| 188.5 | 1.003 | 126 |
| 192 | 1.003 | 126 |
| 195.5 | 1.003 | 126 |
| 199 | 1.003 | 126 |
| 202.5 | 1.002 | 126 |
| 206 | 1.002 | 126 |
| 209.5 | 1.002 | 126 |
| 213 | 1.002 | 126 |
| 216.5 | 1.002 | 126 |
| 220 | 1.002 | 126 |
| 223.5 | 1.002 | 126 |
| 227 | 1.002 | 126 |
| 230.5 | 1.0019 | 126 |
| 234 | 1.0019 | 126 |
| 237.5 | 1.0019 | 126 |
| 241 | 1.0019 | 126 |
| 244.5 | 1.0018 | 126 |
| 248 | 1.0018 | 126 |
| 251.5 | 1.0018 | 126 |
| 255 | 1.0018 | 126 |
| 258.5 | 1.0017 | 126 |
| 262 | 1.0017 | 126 |
| 265.5 | 1.0017 | 126 |
| 269 | 1.0017 | 126 |
| 272.5 | 1.0017 | 126 |
| 276 | 1.0016 | 126 |
| 279.5 | 1.0016 | 126 |
| 283 | 1.0016 | 126 |
| 286.5 | 1.0016 | 126 |
| 290 | 1.0015 | 127 |
| 293.5 | 1.0015 | 127 |
| 297 | 1.0015 | 127 |
| 300.5 | 1.001 | 127 |
| 304 | 1.001 | 127 |
| 307.5 | 1.001 | 127 |
| 311 | 1.001 | 127 |
| 314.5 | 1.001 | 127 |
| 318 | 1.001 | 127 |
| 321.5 | 1.001 | 127 |
| 325 | 1.001 | 127 |
| 328.5 | 1.001 | 127 |
| 332 | 1.001 | 127 |
| 335.5 | 1.001 | 127 |
| 339 | 1.001 | 127 |
| 342.5 | 1.001 | 127 |
| 346 | 1.001 | 127 |
| 349.5 | 1.001 | 127 |
| 353 | 1.001 | 127 |

Fig. 3b

| mV | λ | digital values in the memory |
|---|---|---|
| 356.5 | 1.001 | 127 |
| 360 | 1.001 | 127 |
| 363.5 | 1.001 | 127 |
| 367 | 1.001 | 127 |
| 370.5 | 1.001 | 127 |
| 374 | 1.001 | 127 |
| 377.5 | 1.001 | 127 |
| 381 | 1.001 | 127 |
| 384.5 | 1.001 | 127 |
| 388 | 1.001 | 127 |
| 391.5 | 1.001 | 127 |
| 395 | 1.001 | 127 |
| 398.5 | 1.001 | 127 |
| 402 | 1.001 | 127 |
| 405.5 | 1.001 | 127 |
| 409 | 1.001 | 127 |
| 412.5 | 1.001 | 127 |
| 416 | 1.001 | 127 |
| 419.5 | 1.001 | 127 |
| 423 | 1.001 | 127 |
| 426.5 | 1.001 | 127 |
| 430 | 1 | 128 |
| 433.5 | 1 | 128 |
| 437 | 1 | 128 |
| 440.5 | 1 | 128 |
| 444 | 1 | 128 |
| 447.5 | 1 | 128 |
| 451 | 1 | 128 |
| 454.5 | 1 | 128 |
| 458 | 1 | 128 |
| 461.5 | 1 | 128 |
| 465 | 1 | 128 |
| 468.5 | 1 | 128 |
| 472 | 1 | 128 |
| 475.5 | 1 | 128 |
| 479 | 1 | 128 |
| 482.5 | 1 | 128 |
| 486 | 1 | 128 |
| 489.5 | 1 | 128 |
| 493 | 1 | 128 |
| 496.5 | 1 | 128 |
| 500 | 1 | 128 |
| 503.5 | 1 | 128 |
| 507 | 1 | 128 |
| 510.5 | 1 | 128 |
| 514 | 1 | 128 |
| 517.5 | 1 | 128 |
| 521 | 1 | 128 |
| 524.5 | 1 | 128 |
| 528 | .9999 | 128 |
| 531.5 | .9998 | 128 |
| 535 | .9997 | 128 |
| 538.5 | .9996 | 128 |

Fig. 3c

| | | |
|---|---|---|
| 542 | .9995 | 128 |
| 545.5 | .9994 | 128 |
| 549 | .9993 | 128 |
| 552.5 | .9992 | 128 |
| 556 | .9991 | 128 |
| 559.5 | .999 | 128 |
| 563 | .9989 | 128 |
| 566.5 | .9988 | 128 |
| 570 | .9987 | 128 |
| 573.5 | .9986 | 128 |
| 577 | .9985 | 128 |
| 580.5 | .9982 | 129 |
| 584 | .9979 | 129 |
| 587.5 | .9975 | 129 |
| 591 | .9972 | 129 |
| 594.5 | .9969 | 129 |
| 598 | .9966 | 130 |
| 601.5 | .9963 | 130 |
| 605 | .9959 | 130 |
| 608.5 | .9956 | 130 |
| 612 | .9953 | 130 |
| 615.5 | .995 | 131 |
| 619 | .9946 | 131 |
| 622.5 | .9943 | 131 |
| 626 | .994 | 131 |
| 629.5 | .9936 | 132 |
| 633 | .9932 | 132 |
| 636.5 | .9928 | 132 |
| 640 | .9924 | 132 |
| 643.5 | .992 | 133 |
| 647 | .9916 | 133 |
| 650.5 | .9913 | 133 |
| 654 | .9909 | 133 |
| 657.5 | .9905 | 134 |
| 661 | .9901 | 134 |
| 664.5 | .9897 | 134 |
| 668 | .9893 | 134 |
| 671.5 | .9889 | 135 |
| 675 | .9885 | 135 |
| 678.5 | .9879 | 135 |
| 682 | .9873 | 136 |
| 685.5 | .9867 | 136 |
| 689 | .9861 | 136 |
| 692.5 | .9855 | 137 |
| 696 | .9849 | 137 |
| 699.5 | .9843 | 138 |
| 703 | .9836 | 138 |
| 706.5 | .983 | 138 |
| 710 | .9824 | 139 |
| 713.5 | .9818 | 139 |
| 717 | .9812 | 139 |
| 720.5 | .9806 | 140 |
| 724 | .98 | 140 |

Fig. 3d

| | | |
|---|---|---|
| 727.5 | .979 | 141 |
| 731 | .9785 | 141 |
| 734.5 | .9775 | 142 |
| 738 | .9765 | 142 |
| 741.5 | .9755 | 143 |
| 745 | .974 | 144 |
| 748.5 | .9725 | 145 |
| 752 | .971 | 146 |
| 755.5 | .969 | 147 |
| 759 | .9675 | 148 |
| 762.5 | .9665 | 149 |
| 766 | .9645 | 150 |
| 769.5 | .9625 | 151 |
| 773 | .961 | 152 |
| 776.5 | .958 | 154 |
| 780 | .955 | 156 |
| 783.5 | .952 | 158 |
| 787 | .949 | 160 |
| 790.5 | .946 | 162 |
| 794 | .943 | 164 |
| 797.5 | .94 | 166 |
| 801 | .937 | 168 |
| 804.5 | .9335 | 170 |
| 808 | .929 | 173 |
| 811.5 | .9248 | 175 |
| 815 | .9205 | 178 |
| 818.5 | .9163 | 181 |
| 822 | .9121 | 184 |
| 825.5 | .9079 | 186 |
| 829 | .9036 | 189 |
| 832.5 | .8994 | 192 |
| 836 | .8952 | 194 |
| 839.5 | .8909 | 197 |
| 843 | .8867 | 200 |
| 846.5 | .8825 | 202 |
| 850 | .8782 | 205 |
| 853.5 | .874 | 208 |
| 857 | .866 | 213 |
| 860.5 | .862 | 215 |
| 864 | .8549 | 220 |
| 867.5 | .8478 | 225 |
| 871 | .8407 | 229 |
| 874.5 | .8336 | 234 |
| 878 | .8265 | 238 |
| 881.5 | .8194 | 243 |
| 885 | .8123 | 247 |
| 888.5 | .8052 | 252 |
| 892 | .7981 | 255 |
| 895.5 | .791 | |

Fig. 3e

METHOD AND DEVICE FOR IMPROVING THE EXHAUST-GAS BEHAVIOR OR MIXTURE-COMPRESSING INTERNAL COMBUSTION ENGINES

BACKGROUND OF THE INVENTION

The present invention relates to a method of improving the exhaust-gas behavior of mixture-comprising internal combustion engines, in which the output signal of an oxygen measurement probe arranged in the exhaust gas channel of the internal combustion engine is fed to a controller the output voltage of which represents a setting variable for controlling the fuel-air ratio.

The invention furthermore relates to a device for the carrying out of the method.

In the art of preparing the fuel-air mixture for mixture-compressing internal combustion engines, it has been known for a long time to control the composition of the mixture as a function of the output signal of an oxygen measurement probe arranged in the stream of exhaust-gas in order to achieve the best possible elimination of noxious exhaust gases. In this case, the output signal of the oxygen measurement probe is fed to a controller, and the output voltage of the controller forms a setting variable for controlling the fuel-air ratio.

By the control of the fuel-air ratio of internal combustion engines, it is desired primarily to reduce noxious contents of the exhaust-gas emissions of internal combustion engines. For this purpose, a method is known, for instance, which employs an oxygen measurement probe arranged in the exhaust-gas stream of the internal combustion engine and controls an integrating device, the output signal of the exhaust-gas measurement probe being applied to a threshold switch, and switching the latter when the threshold valve is reached. The direction of integration of the integrating device is changed upon the switching of the threshold switch. The time constant of the integrating device is changed as a function of at least one operating parameter of the internal combustion engine, and particularly as a function of the amount of intake air of the internal combustion engine. The integrating device of variable time constant proposed in the case of the known method, however, does not satisfy all requirements with respect to precise and adaptable control. In particular, in the known method the setting variable does not follow sudden changes in loads sufficiently rapidly.

The voltage signal of an oxygen measurement probe typically has a steep course, in the region of lambda=1, which passes in each case into a flat branch directly adjoining this region. The voltage signal of the oxygen measurement probe acts on the means for forming the mixture in the manner that upon a signal from the probe which corresponds to a lambda of less than 1, the mixture is made leaner, while with a probe signal of more than 1, the mixture is made richer. As a result of the steep course of the characteristic curve, the control passes in quasi-steady state continuously through the region of the characteristic curve between the two points of inflection. On the average, the compostion of the mixture is such that it corresponds to the stoichiometric value and the exhaust gas can be substantially freed of undesired noxious portions by a catalytic exhaust-gas purification device.

Upon a sudden change in load, such as occurs frequently in the normal travel of an automotive vehicle, the value of the fuel-air ratio, lambda, can differ considerably from the desired value 1, primarily as a result of condensation processes in the intake region of the internal combustion engine. As a result of the flat course of the characteristic curve of the voltage value of the oxygen measurement probe with lambda values above or below a value of 1, however, only a relatively small disturbance signal is produced so that the control device only inadequately recognizes the actual deviation of the lambda value from the desired condition. Accordingly, the return of the control to the value of 1 takes an undesiredly long period of time and, during this time, the exhaust gases contain a high percentage of noxious substances. Furthermore, the continuous variation of the fuel-air ratio within relatively wide limits around a value of 1 results in a periodic change in the composition of the exhaust gas which must be counteracted in the following manner, namely, that both the exhaust-gas measurement probe and the catalytic aftertreatment device for the purification of the exhaust gas are arranged at a minimum distance from the outlet of the internal combustion engine.

A method is already known in which a regulation in accordance with a stored typical field of characteristic curves is superimposed on the control of the fuel-air ratio. However, this method does not eliminate the difficulties inherent in the nonlinear course of the characteristic curve of the oxygen measurement probe. Furthermore, there is a considerable expense for memory in the electronic regulating device.

SUMMARY OF THE INVENTION

It is an object of the invention to provide a method of improving the exhaust-gas behavior of mixture-comprising internal combustion engines which, upon quasi-steady operation, permits a stable control of the excess fuel-air ratio, lambda, at the value 1. Furthermore, the fuel-air-mixture forming device in question is to be capable of rapidly counteractig disturbances in the composition of the mixure due to changes in the operation conditions of the internal combustion engine so that the time span within which the mixture-forming device permits exhaust gases having a high proportion of noxious substances is shorter than in devices of the prior art.

According to the invention, the voltage range of the output signal of the oxygen measurement probe is divided into a fixed number of individual steps, a corrected voltage value is stored in a memory for each individual step, and the corrected voltage values are taken as basis for the further processing of the signal.

Further according to the invention, there is provided for the carrying out of the method a device which has a read-only memory to the input of which the analog-digital converted output signal of the oxygen measurement probe is fed, and which experiences a change by a correction table stored in the read-only memory. At the output of the memory there is obtained the changed probe signal which is fed then to the input of a controller for controlling the composition of the fuel-air mixture, possibly after digitial-analog conversion.

In this connection, there is the advantage that the stability of the control of the mixture-forming measurement device on the whole becomes better. There is also the advantage that disturbances due to changes in the operating parameters of the internal combustion engine can be counteracted faster and that, furthrmore, the brief deviations in cotrol in this connection are less than in the case of the known devices.

The method of the invention is suitable for different fuel-injection systems such as, for instance, continuously or intermittently injecting systems with central or cylinder injection. Accordingly, the setting variable given off by the controller can regulate the pressure or the duration of injection of the fuel in the injection system.

According to a feature of the invention, the analog output signal of the oxygen measurement probe is converted by an analog-digital conversion into a digital signal, a correction table for each detectable value of the probe output signal is stored in a read-only memory, and the corrected signal from the output of the read-only memory is used for contolling the gas mixture.

According to another feature of the invention, the corrected voltage values result referred to the actual fuel-air ratio, lambda, in a selectable course of the characteristic curve.

Still further according to the invention, the corrected voltage values referred to the actual fuel-air ratio, lambda, give a linear course of the characteristic curves.

Yet further according to the invention, the corrected voltage values referred to the actual fuel-air ratio, lambda, give a progressive course of the characteristic curve on both sides of the fuel-air ratio, lambda = 1.

BRIEF DESCRIPTION OF THE DRAWINGS

With the above and other objects and advantages in view, the present invention will become more clearly understood in connection with the detailed description of a preferred embodiment, when considered with the accompanying drawings, in which:

FIGS. 3a, 3b, 3c, 3d and 3e are numerical examples of a change of this characteristic curve in tabular form;

DETAILED DESCRIPTION OF THE PREFERRED EMBODIMENT

Figure 1:
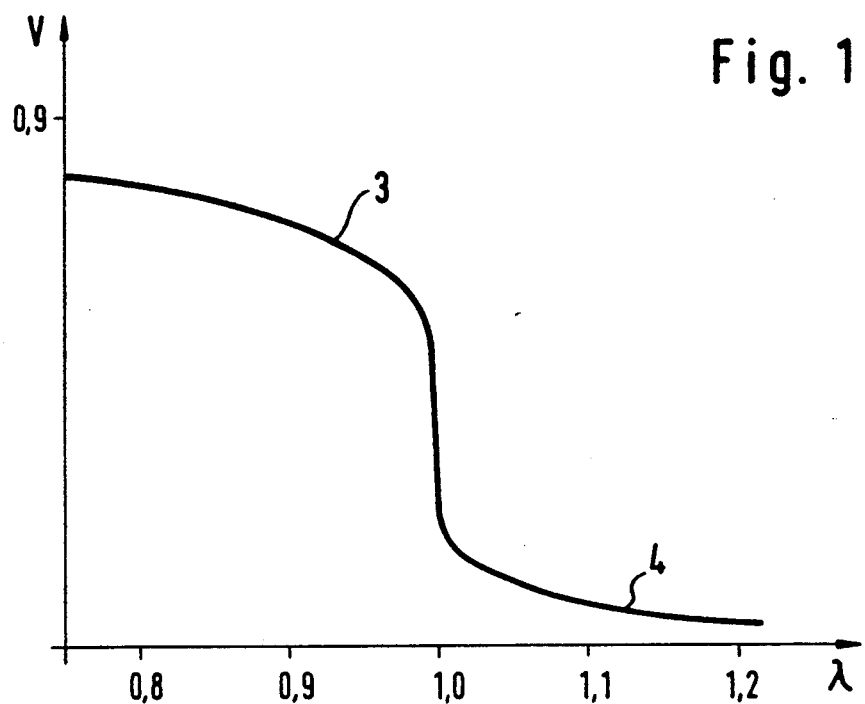
FIG. 1 is a graph of voltage vs. fuel-air ratio of an oxygen measurement probe.

FIG. 1 shows a graph of the output signal of an oxygen measurement probe such as is arranged in the exhaust-gas channel of an internal combustion engine in order to detect the composition of the exhaust gas. The oxygen measurement probe is typically a zirconium oxide probe the output signal of which is between a few millivolts for a fuel-air ratio, lambda, which is definitely greater than 1 and about 900 millivolts for a fuel-air ratio which is definitely smaller than 1. In this connection, there is obtained a flat course of the characteristic curve in the regions above and below the stoichiometric value 1, while in a very narrow range around lambda = 1, the voltage changes by several hundred millivolts. Since for the proper operation of a catalytic exhaust-gas aftertreatment device, it is necessary to keep the value of the fuel-air ratio close to 1, relatively large variations in the probe voltage are produced upon merely slight changes in the value of the number lambda.

Accordingly, continuous control cannot be obtained, but a sort of two-point control is developed, the lambda value oscillating rapidly around the value 1 so that the composition of the exhaust gas is, on the average, in accord with the requirements. In this connection, the control slope cannot be made of just any size since, in such case, the system becomes unstable. On the other hand, in case of changes in load, the control takes place only slowly and the fuel-air mixture deviates temporarily from the stoichiometric value. In this way, the catalytic aftertreatment takes place incompletely and the proportion of noxious comonents in the exhaust gas increases in undesired fashion. This delayed control is furthermore effected by the flat course of the two sections 3 and 4 of the characteristic curve since, even upon considerable deviations from the desired value of 1 of the number lambda, the output voltage of the probe changes only slightly, so that the recognition of large changes affords difficulties.

Figure 2:
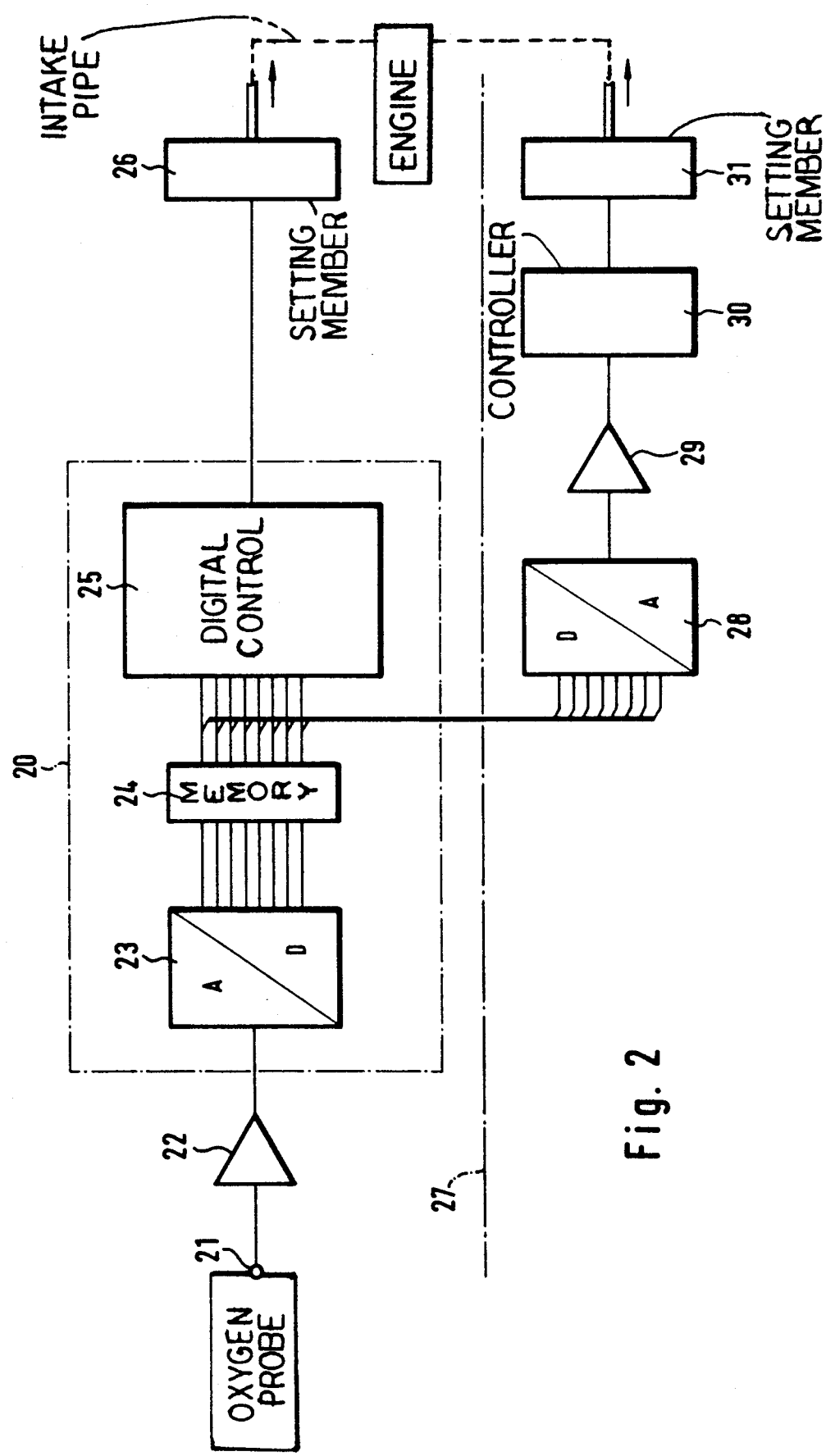
FIG. 2 is a circuit diagram showing the basic circuit for varying the characteristic curve of an oxygen measurement probe, insofar as this is essential for the invention.

FIG. 2, the output of the oxygen measurement probe is designated 21. The signal present there is amplified in an input amplifier 22 and converted in a A/D converter 23 for the conversion of the analog signal value into digital data. The latter are fed in parallel to a memory device 24 in which correction values which change the characteristic curve of the oxygen measurement probe in desired fashion are stored in a read-only memory. For example, it may be desired to linearize the characteristic curve in order to obtain a proportional relationship between the fuel-air ratio, lambda, and the signal voltage. However, by simple change of the correction values it is also possible to impart to the characteristic curve a progressive course starting from the value lambda = 1 in order to improve the quality of the control as a whole. Thus, with increasing deviation of the fuel-air ratio, lambda, from the desired value, a considerably greater increase in the proportional share of the return takes place and automatically declines after a counteracting of the disturbance. In this way, the stability of the control is generally increased. The probe signal which is processed in the device 24 then passes for further processing into a digital control device 25, from where it is passed in suitable form to a setting member 26 which controls the composition of the mixture of the internal combustion engine. The electric components 23, 24, 25 can also be combined in a single electric component 20.

Below the dash-dot line 27 in FIG. 2, there is shown, as alternative, an analog signal processing of the probe signal from which the distortion is removed in the device 24. The signal is first of all fed to a D/A-converter 28 for reconversion of the digital signal into an analog signal, and the latter is raised, via another amplifier 29, to a voltage level suitable for processing by a following contoller 30. The controller 30 furthermore acts on a setting member 31 which, as shown in the upper half of FIG. 2, acts on the composition of the mixture of the internal combustion engine in such a manner that the fuel-air ratio, lambda, is kept as close as possible to a value of 1.

FIG. 3 shows in tubular form the appearance of stored values in the event that the probe voltage is to be brought into a substantially linear relationship to the value of the measured air number lambda. In this connection, the first numerical column gives the probe voltage which is used to address the memory device 24.

The probe voltage is generated at the lambda value which is printed horizontally alongside of it in the second column. The mumerical columns 36 and 37 show, opposite each other, the desired linear relationship between the processed probe signal and the fuel-air ratio lambda. The numerical column 35 shows the corresponding voltage of the oxygen measurement probe.

Figure 4:
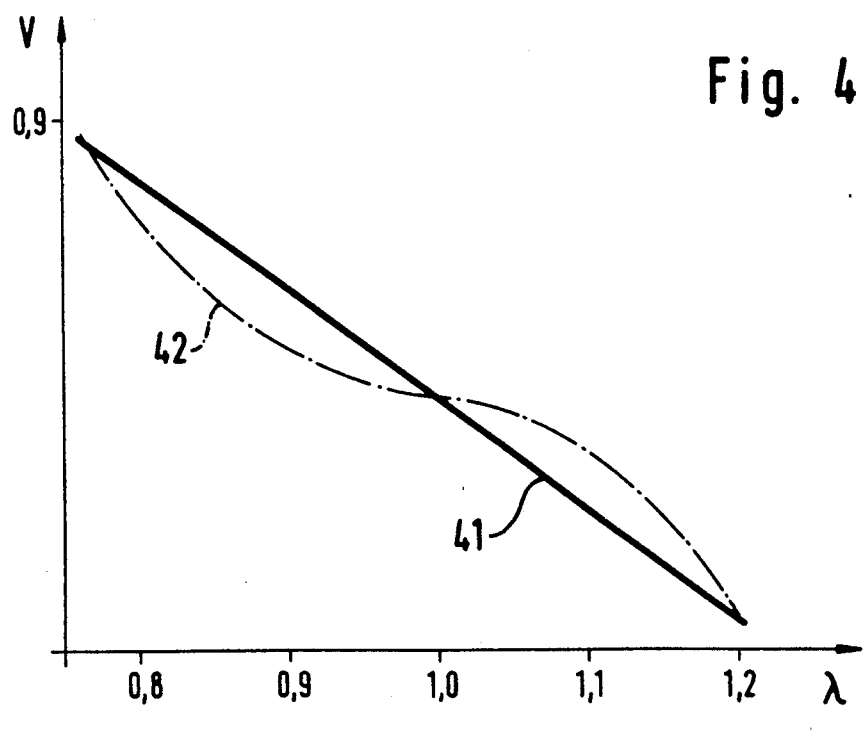
FIG. 4 is, for instance, a corrected voltage vs. fuel-air ratio graph of an oxygen measurement probe.

FIG. 4 shows, by way of example, two possible ways in which the output signal of the oxygen measurement probe can advantageously be modified. The curve 41 represents a linear relationship between the value of the number lambda and the voltage value, while the curve 42 shows a progressive course towards both sides, starting from the lambda equal to 1.

Figure 5:
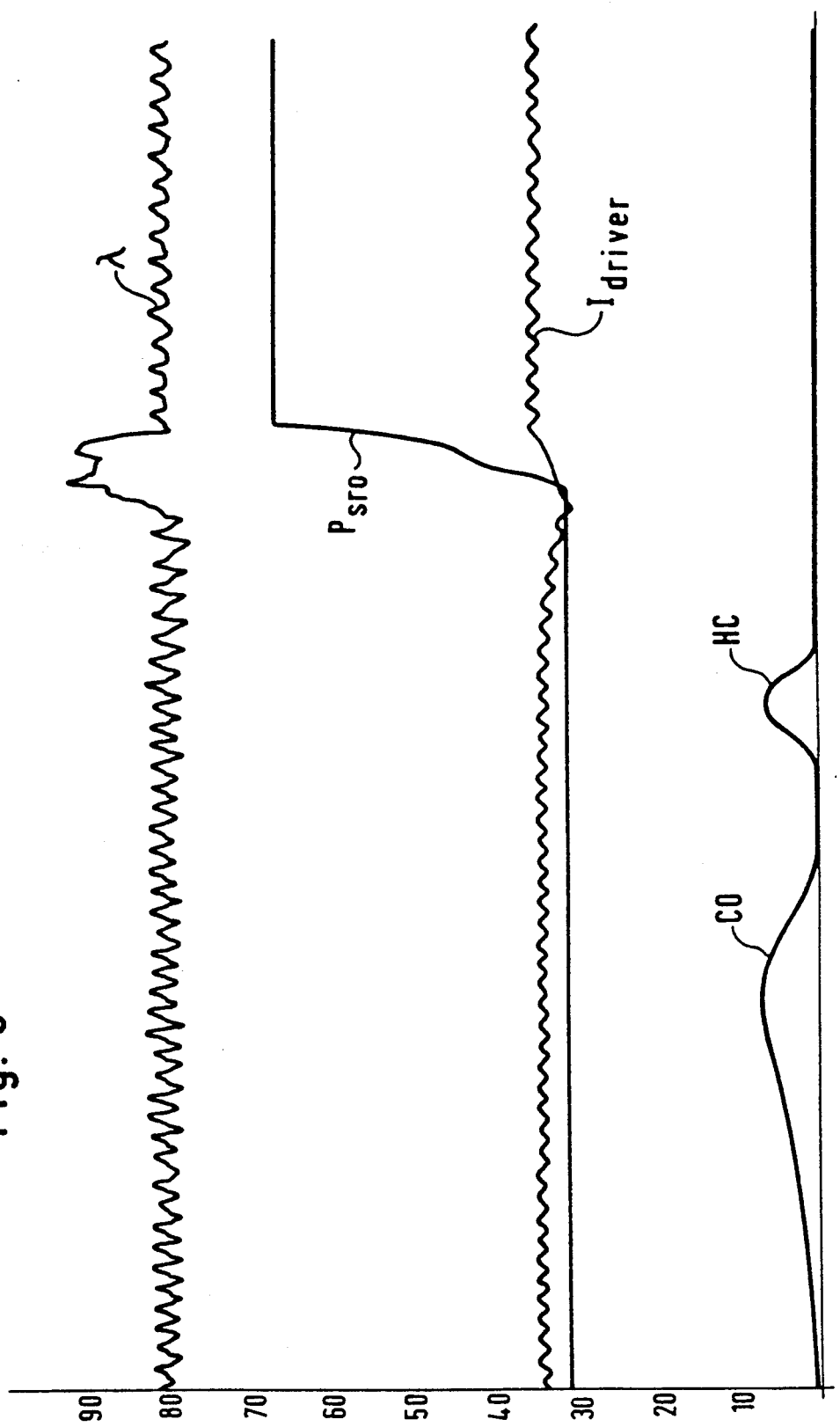
FIG. 5 is a graph showing the jump response of a known fuel-air mixture forming device.

FIG. 5 shows how lambda responds to a change in load of an internal combustion engine. The change in load is characterized by the change in the intake pipe pressure $P_{sro}$. As a result of the relationships described at the start, the deviation of lambda from the value of 1 is counteracted only slowly. The build-up process for the current at the setting member ($I_{driver}$) takes a correspondingly long period of time. At the lower edge of FIG. 5, the proportions of noxious substances in the exhaust gas as shown in the form of curves. Both the proportion of unburned hydrocdarbons HC and of carbon monoxide CO differ for a lengthy period of time from the desired value of zero.

Figure 6:
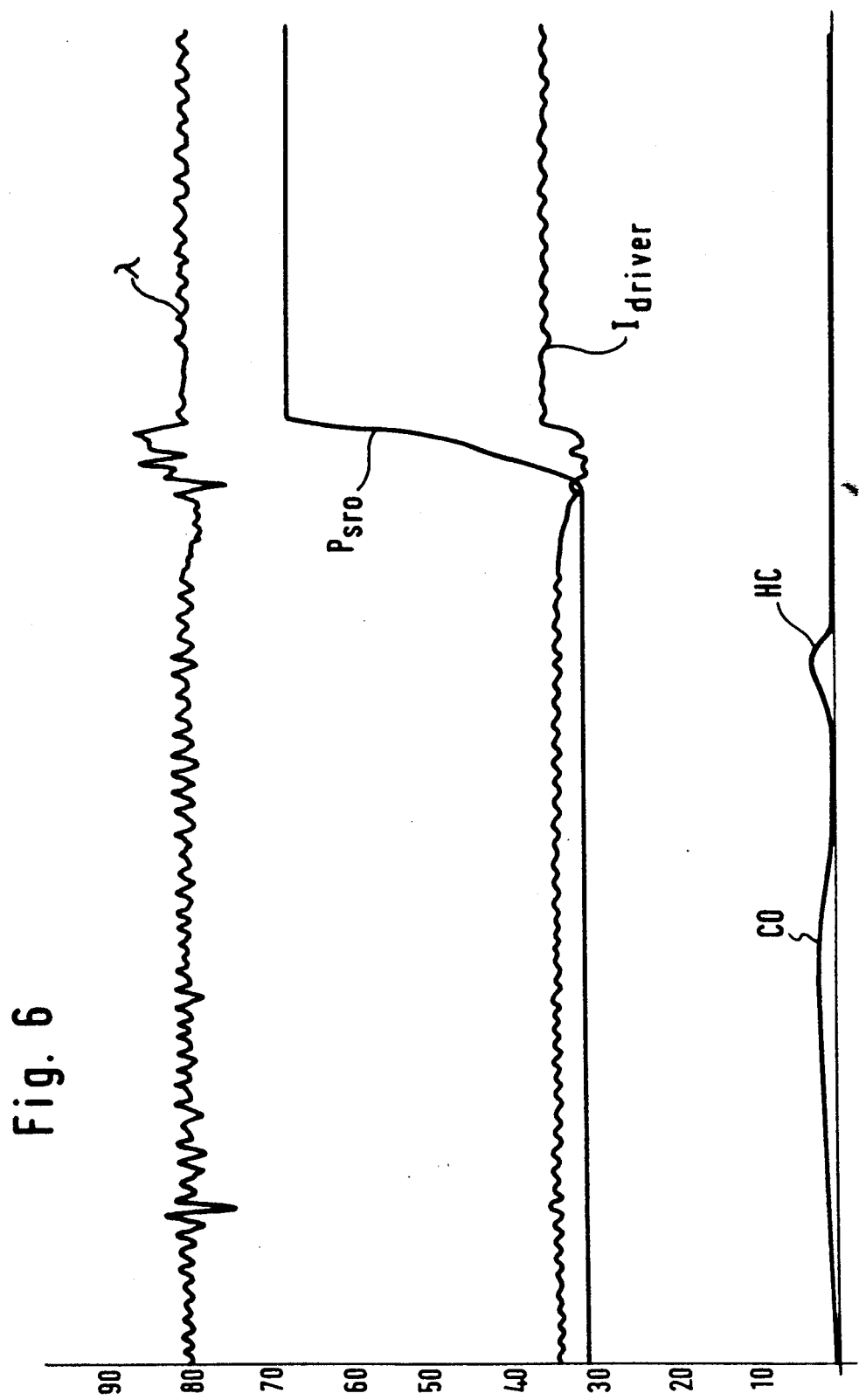
FIG. 6 is a graph showing the jump response of the fuel-air-mixture forming device of the invention, in each case for the same change in load of the internal combustion engine.

In contradistinction to this, FIG. 6, which shows the recording for the method of the invention with the use of the device of the invention, the deviation from lambda with a similar change of the intake pipe pressure $P_{sro}$ is considerably less than in the known arrangement corresponding to FIG. 5a. Similarly, the build-up time for the setting current $I_{driver}$ is substantially shorter and the deviations of the curves for the noxious substances HC and CO in the exhaust gas less.

We claim:

1. A method for improving the exhaust-gas behavior of mixture-comprising internal combustion engines, the engine being operative with a controller, there being an oxygen measurement probe, disposed in an exhaust channel of the engine, the method comprising the steps of
   feeding the output signal of the probe to the controller, the output voltage of the controller respresenting a setting variable for controlling the fuel-air ratio of the engine.
   dividing the voltage range of an output signal of the probe into a fixed number of individual steps,
   storing a corrected voltage value in a memory for each of said steps, and
   employing the corrected voltage values as a basis for a further processing of the signal.

2. The method according to claim 1, further comprising the steps of
   converting the analog output signal of the oxygen measurement probe by an analog-digital conversion into a digital signal;
   said storing step employs a correction table for each detectable value of the probe output signal, the table being stored in a read-only memory; and
   using the corrected signal from the output of the read-only memory for controlling the gas mixture.

3. The method according to claim 2, wherein
   the corrected voltage values are referred to the actual fuel-air ratio in a selectable course of the characteristic curve.

4. The method according to claim 1, wherein
   the corrected voltage values are referred to the actual fuel-air ratio in a selectable course of the characteristic curve.

5. The method according to claim 2, wherein
   the corrected voltage values are referred to the actual fuel-air ratio to give a linear course of the characteristic curves.

6. The method according to claim 2, wherein
   the corrected voltage values referred to the actual fuel-air ratio give a progressive course of the characteristic curve on both sides of the fuel-air ratio, lambda = 1.

7. A device for linearizing fuel-air ratio measurements of an oxygen probe for an internal combustion engine comprising;
   an analog-to-digital converter, a read-only memory, and a controller, the converter connecting an oxygen probe to an imput of the memory for addressing the memory to output a correct value of an oxygen measurement of the probe; and
   wherein a correction table is stored in the read-only memory, and at the output of the memory there is obtained a changed probe signal which is fed to an input of the controller for controlling the composition of the fuel-air mixture.

8. A device according to claim 7, wherein
   said controller operates on analog signals, said device further comprising
   a digital-to-analog converter connecting an output of the memory to an input of the controller for converting digital signals of the memory to analog format.

* * * * *